United States Patent
Hoshino et al.

(10) Patent No.: US 9,632,081 B2
(45) Date of Patent: Apr. 25, 2017

(54) DETECTION METHOD FOR BIOLOGICAL SUBSTANCE

(71) Applicants: Konica Minolta, Inc., Tokyo (JP); Tohoku University, Sendai-shi, Miyagi (JP)

(72) Inventors: Hideki Hoshino, Kokubunji (JP); Hideki Gouda, Tokyo (JP); Kensaku Takanashi, Hachioji (JP); Yasushi Nakano, Hino (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/386,546

(22) PCT Filed: Mar. 25, 2013

(86) PCT No.: PCT/JP2013/058607
§ 371 (c)(1),
(2) Date: Sep. 19, 2014

(87) PCT Pub. No.: WO2013/146694
PCT Pub. Date: Oct. 3, 2013

(65) Prior Publication Data
US 2015/0051101 A1  Feb. 19, 2015

(30) Foreign Application Priority Data

Mar. 28, 2012 (JP) ................................. 2012-074216

(51) Int. Cl.
| | | |
|---|---|---|
| C12Q 1/68 | (2006.01) | |
| C12M 1/34 | (2006.01) | |
| G01N 33/53 | (2006.01) | |
| G01N 1/30 | (2006.01) | |
| G01N 33/48 | (2006.01) | |
| C07H 21/04 | (2006.01) | |
| C40B 30/04 | (2006.01) | |
| C40B 40/06 | (2006.01) | |
| G01N 31/22 | (2006.01) | |
| G01N 33/543 | (2006.01) | |
| G01N 33/574 | (2006.01) | |
| G01N 33/58 | (2006.01) | |

(52) U.S. Cl.
CPC ... *G01N 33/54393* (2013.01); *G01N 33/5306* (2013.01); *G01N 33/54346* (2013.01); *G01N 33/57415* (2013.01); *G01N 33/57492* (2013.01); *G01N 33/582* (2013.01); *G01N 33/587* (2013.01)

(58) Field of Classification Search
CPC ...... G01N 31/22; G01N 33/567; C07H 21/04; C12M 1/34; C12Q 1/68
USPC ............ 435/6.1, 7.1, 40.52; 536/23.1, 24.3; 506/9, 16; 422/430
See application file for complete search history.

(56) References Cited

U.S. PATENT DOCUMENTS

| | | | | |
|---|---|---|---|---|
| 5,840,485 | A * | 11/1998 | Lebl | C07K 1/047 435/6.1 |
| 2004/0101822 | A1 | 5/2004 | Wiesner et al. | |
| 2009/0017561 | A1 * | 1/2009 | Aizawa | B82Y 15/00 436/514 |
| 2009/0110644 | A1 * | 4/2009 | Margel | A61K 41/0052 424/9.322 |
| 2013/0039848 | A1 * | 2/2013 | Bradbury | A61K 49/0019 424/1.37 |
| 2013/0157287 | A1 * | 6/2013 | Takanashi | G01N 21/6428 435/7.1 |
| 2013/0157895 | A1 * | 6/2013 | Aimiya | G01N 1/30 506/9 |

FOREIGN PATENT DOCUMENTS

| | | | |
|---|---|---|---|
| JP | 3-216554 A | | 9/1991 |
| JP | 2005-281019 A | | 10/2005 |
| JP | 2009-115822 A | | 5/2009 |
| JP | 2010-112748 A | | 5/2010 |
| JP | WO 2012/029342 | * | 3/2012 |
| WO | WO2012/029752 A1 | | 3/2012 |

OTHER PUBLICATIONS

Machine Translation of JP2010-112748 A, Description Part A, pp. 8-19, printed on Dec. 15, 2015.*
Canning et al, Percolation Diffusion into Self-Assembled Mesoporous Silica Microfibres, 2014, Nanomaterials, 4, 1-18.*
Zhou X, et al: "Improving the Signal Sensitivity and Photostability of DNA Hybridizations on Microarrays by Using Dye-Doped Core-Shell Silica Nanoparticles" Analytical Chemistry, American Chemical Society, US vol. 76, No. 18, Sep. 15, 2004, pp. 5302-5312.
Pathology and clinical medicine; vol. 25; 2007 extra issue; Immunohistochemistry useful for diagnoses; Bunkodo Co., Ltd.
Notification of Reasons for Refusal dated Feb. 7, 2017 from the corresponding Japanese Application No. 2014-507869; English translation of Notification of Reasons for Refusal; Total of 5 pages.

* cited by examiner

*Primary Examiner* — Narayan Bhat
(74) *Attorney, Agent, or Firm* — Lucas & Mercanti, LLP

(57) ABSTRACT

A detection method for a specific biological substance uses, as a color former, fluorescent substance-encapsulated nanoparticles which have biological substance-recognizing molecules. The biological substance-recognizing molecules specifically recognize a specific biological substance. The biological substance-recognizing molecules are bonded to the surface of the nanoparticles. Nanoparticles encapsulating no fluorescent substance are used as a blocking agent for preventing the fluorescent substance-encapsulated nanoparticles from being non-specifically adsorbed on a biological substance other than the specific biological substance.

2 Claims, No Drawings

DETECTION METHOD FOR BIOLOGICAL SUBSTANCE

CROSS REFERENCE TO RELATED APPLICATION

This Application is a 371 of PCT/JP2013/058607 filed on Mar. 25, 2013 which, in turn, claimed the priority of Japanese Patent Application No. JP2012-074216 filed on Mar. 28, 2012 both applications are incorporated herein by reference.

TECHNICAL FIELD

The present invention relates to a detection method for a biological substance. More particularly, the present invention relates to a detection method for a biological substance, which uses fluorescent substance-encapsulated nanoparticles and nanoparticles encapsulating no fluorescent substance in combination.

BACKGROUND ART

Cancers are diseases that halve the causes of deaths of adults with vascular diseases such as myocardial infarction and cerebral infarction. For example, prevalence of breast cancer in Japan is lower than that in Western countries, but it tends to increase in recent years, and in 1998, the prevalence of breast cancer moved into first place of the disease prevalence in a female, past that of stomach cancer. According to the Statistical Survey by Ministry of Health, Labor and Welfare in 2005 that is the recent report, the number of affected individuals with breast cancer per year exceeded 50,000. Also in the world, the number thereof is increasing year by year, and according to the report by WHO in 2008, the prevalence of breast cancer took first place in both of a male and a female, the number of the affected individuals per year exceeded 1,380,000, and the female breast cancer patients occupy about 23% of the whole of the female cancer patients.

For diagnoses of cancers, not only imaging diagnoses such as X-ray CT and MRI but also methods of detecting a cancer marker that is specifically expressed in a specific cancer, a cancer marker that leaks into blood or tissue, etc. have been widely used. When medical examination by interview, palpation, soft X-ray breast imaging (mammography), echography, etc. are carried out as general screening tests for breast cancer and cancer is clinically suspected, cytodiagnosis or biopsy is conducted, and pathological diagnosis is made to judge whether it is cancer or not. In order to decide cancer treatment or prognosis, the pathological diagnosis is important, and in this diagnosis, "HE [hematoxylineosin] staining method for carrying out morphological observation" and "immunohistochemical method using antibody to cancer marker factor" are mainly used. In particular, by the emergence of antibody preparations in recent years, importance of the immunohistochemistry has been extremely increased. For example, it is known that Trastuzumab, which is on the market under the name of Herceptin (registered trademark) that is an antibody preparation targeting a human epidermal growth factor receptor-2 [HER2] serving as a factor participating in cancer growth, is a typical anticancer drug for breast cancer. As methods to judge the efficacy of administration of this drug, an immunohistochemistry [IHC] method that analyzes expression of HER2 protein, etc. and a FISH [fluorescence in situ hybridization] method that analyzes amplification of HER2 gene, etc. are widely used in the clinical field. In the IHC method, a HER2 antibody bonded to a HER2 antigen site is stained with DAB [diaminobenzidine] to visualize it, whereby the quantity of HER2 expression can be detected. However, since the judgment criteria are rough criteria in which stained levels are divided into only four stages of scores 0 to 3, the method is lacking in quantitativity, and the judgment criteria depend upon proficiency of a pathologist, so that this method clinically has a problem. On the other hand, the FISH method is carried out using a probe for detecting a HER2 gene and a probe for detecting chromosome 17 centromere, and on the basis of the number of HER2 gene copies per chromosome 17 analyzed by this FISH method, presence or absence of amplification of the HER2 gene can be judged. The FISH method is a quantitative testing method, but it is not a method for directly evaluating the quantity of HER2 protein or intracellular localization of HER2. In such circumstances, development of a highly precise method for judging the efficacy of a drug containing an antibody as a component has been needed.

In view of such circumstances, a method for judging presence or absence of a target molecule by bonding a fluorescent substance such as a fluorescent dye or semiconductor nanoparticle to an antibody has been carried out. The fluorescent staining has a feature of excellent quantitativity as compared with DAB staining (non patent literature 1). However, general fluorescent dyes and semiconductor nanoparticles emit small quantities of fluorescence, and therefore, unless intrinsic fluorescence is properly separated and removed, judgment of target molecule due to fluorescence cannot be made, so that for the morphological information, HE staining of another section is necessary.

For such a reason, a method for increasing the quantity of fluorescence based on one labeled material by incorporating a fluorescent dye or semiconductor nanoparticles was thought. For example, in a patent literature 1, there are disclosed glass fluorescent substance nanoparticles in each of which semiconductor nanoparticles are dispersed and fixed by combining a reverse micelle method with a sol-gel method using, as a glass precursor, a mixture of organoalkoxysilane and alkoxide, said organoalkoxysilane having, at the molecular end, an organic functional group of good adsorptivity on semiconductor nanoparticles. In such means, the quantity of fluorescence is increased and judgment of target molecule becomes possible, but even slight occurrence of non-specific bonding becomes a cause of increase in background noise, and therefore, this has become a serious problem in high-sensitivity determination and detection.

CITATION LIST

Patent Literature

Patent literature 1: Japanese Patent Laid-Open Publication No. 2005-281019

Non Patent Literature

Non patent literature 1: "Pathology and Clinical Medicine, Vol. 25, 2007 extra issue, Immunohistochemistry useful for diagnoses", edited on Mar. 12, 2007, Bunkodo Co., Ltd.

SUMMARY OF INVENTION

Technical Problem

The present invention has been made in view of the above problem, and it is an object of the present invention to provide a detection method in which background noise is not increased even if a high-luminance fluorescent labeling material is used and which has an improved S/N ratio and high quantitativity and is advantageous for an immunohistological staining method.

Solution to Problem

In order to achieve the above object, the present inventors have earnestly studied. As a result, they have found that in an immunohistological staining method using fluorescent substance-encapsulated nanoparticles as a color former, nanoparticles encapsulating no fluorescent substance are significantly superior in blocking ability to bovine serum albumin [BSA] that is usually used as a blocking agent, and they have accomplished the present invention.

That is to say, the detection method of the present invention to realize at least one of the aforesaid objects is, in one aspect, a detection method for a specific biological substance, which uses, as a color former, fluorescent substance-encapsulated nanoparticles to whose particle surfaces biological substance-recognizing molecules that specifically recognize a specific biological substance have been bonded, wherein nanoparticles encapsulating no fluorescent substance are used as a blocking agent for preventing the fluorescent substance-encapsulated nanoparticles from being non-specifically adsorbed on a biological substance other than the specific biological substance.

Advantageous Effects of Invention

According to the present invention, by using high-luminance fluorescent substance-encapsulated nanoparticles as a color former and by using nanoparticles encapsulating no fluorescent substance as a blocking agent in the detection of a specific biological substance, a histologically stained image having an improved S/N ratio can be observed, and accuracy of diagnosis by a pathologist can be enhanced.

The reason why the nanoparticles encapsulating no fluorescent substance favorably function as a blocking agent in the present invention is thought to be that non-specific adsorption, which occurs depending upon the composition of a matrix for constituting the nanoparticles, the organic molecules for coating the surfaces of the nanoparticles, the size of the nanoparticles, etc., can be prevented by the blocking agent in the present invention, while a conventional blocking agent for protein, such as BSA, prevents non-specific adsorption concerning the antigen-antibody reaction (hence, non-specific adsorption of antibody or the like bonded to the fluorescent substance-encapsulated nanoparticles can be prevented).

DESCRIPTION OF EMBODIMENTS

The method for detecting a specific biological substance according to the present invention will be described in detail hereinafter.

The present invention is a method for detecting a specific biological substance, which uses, as a color former, fluorescent substance-encapsulated nanoparticles to whose particle surfaces biological substance-recognizing molecules that specifically recognize a specific biological substance have been bonded, wherein nonoparticles encapsulating no fluorescent substance are used as a blocking agent for preventing the fluorescent substance-encapsulated nanoparticles from being non-specifically adsorbed on a biological substance other than the specific biological substance.

Method for Detecting Specific Biological Substance

Specific examples of the methods for detecting a specific biological substance according to the present invention include immunochromatography, immunoassay, western blotting method, northern blotting method, southern blotting method, hybridization method using DNA array (or DNA microarray or DNA chip), immunohistochemical method and immunocytochemical method. Of these, a method of fluorescent staining a tissue section is preferable, and an immunohistochemical method is particularly preferable.

Fluorescent Substance

As the fluorescent substances for use in the present invention, fluorescent materials containing fluorescent organic dyes or semiconductor nanoparticles can be mentioned. Preferable are fluorescent substances that emit visible to near infrared light in the wavelength region of 400 to 900 nm when they are excited with ultraviolet to near infrared light in the wavelength region of 200 to 700 nm.

(Organic Fluorescent Dye)

Examples of the organic fluorescent dyes include fluorescein-based dye molecules, rhodamine-based dye molecules, Alexa Fluor (manufactured by Invitrogen)-based dye molecules, BODIPY (manufactured by Invitrogen)-based dye molecules, Cascade-based dye molecules, coumarin-based dye molecules, eosin-based dye molecules, NBD-based dye molecules, pyrene-based dye molecules, Texas Red-based dye molecules and cyanine-based dye molecules.

Specifically, there can be mentioned 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2', 7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650 and BODIPY 650/665 (these are manufactured by Invitrogen), methoxycoumarin, eosin, NBD, pyrene, Cy5, Cy5.5, Cy7, etc. The organic fluorescent dyes may be used singly or in combination of two or more kinds.

(Semiconductor Nanoparticles)

The semiconductor nanoparticle for use in the present invention has a core/shell structure, is a particle containing the later-described material (raw material) for forming a semiconductor and having a particle diameter of nanosize (1 to 1,000 nm), and is a particle having a multiple structure constituted of a core (center portion) and a shell (coating portion) for coating the core. Any one of a semiconductor nanoparticle containing a II-VI Group compound as a component, a semiconductor nanoparticle containing a III-V Group compound as a component and a semiconductor nanoparticle containing a IV Group element as a component (also referred to as "II-VI Group semiconductor nanoparticle", "III-V Group semiconductor nanoparticle" and "IV Group semiconductor nanoparticle", respectively) can be used, and they may be used singly or in combination of two or more kinds.

As the materials for forming the core (also referred to as a "core particle"), semiconductors, such as silicon [Si], germanium [Ge], indium nitride [InN], indium phohsphide [InP],gallium arsenide [GaAs], aluminum selenide [AlSe], cadmium selenide [CdSe], aluminum arsenide [AlAs], gallium phosphide [GaAs], zinc telluride [ZnTe], cadmium telluride [CdTe], indium arsenide [InAs] and indium-gallium-phosphorus [InGaP], or raw materials for forming them can be used. In particular, InP, CdTe or CdSe is more preferably used in the present invention.

As the materials for forming the shell, inorganic semiconductors of II-VI Group, III-V Group and IV Group can be used. Preferable are semiconductors having higher band gap than the core-forming inorganic materials such as Si, Ge, InN, InP, GaAs, AlSe, CdSe, AlAs, GaP, ZnTe, CdTe and InAs and having no toxicity, or materials for forming them. For the core of InP, CdTe or CdSe, ZnS is more preferably applied to the shell.

In the present specification, the semiconductor nanoparticle is sometimes represented in the following manner. For example, when the material of the core is CdSe and the material of the shell is ZnS, the semiconductor nanoparticle is sometimes represented by "CdSe/ZnS".

Examples of the semiconductor nanoparticles include CdSe/ZnS, CdS/ZnS, InP/ZnS, InGaP/ZnS, Si/SiO$_2$, Si/ZnS, Ge/GeO$_2$ and Ge/ZnS, but the present invention is not limited thereto.

As the semiconductor nanoparticles, semiconductor nanoparticles having been subjected to surface treatment with an organic polymer or the like may be used, when needed. Examples of such semiconductor nanoparticles include CdSe/ZnS having surface carboxyl group (manufactured by Invitrogen) and CdSe/ZnS having surface amino group (manufactured by Invitrogen).

Fluorescent Substance-Encapsulated Nanoparticles, Nanoparticles Encapsulating No Fluorescent Substance The fluorescent substance-encapsulated nanoparticle for use in the present invention is a nanoparticle in which a fluorescent substance is dispersed, and a material (sometimes also referred to as a "matrix" in the present invention) that constitutes the nanoparticle and the fluorescent substance may be or may not be chemically bonded to each other. On the other hand, the nanoparticle encapsulating no fluorescent substance, which is used as a blocking agent in the present invention, is a nanoparticle in which a fluorescent substance is not contained, and is typically a nanoparticle composed of only such a matrix as described above.

The material to constitute the nanoparticle is not specifically restricted, and is, for example, silica, melamine, polystyrene or polylactic acid. Such materials may be used singly or in combination of two or more kinds. In the present invention, a nanoparticle whose matrix is composed of silica is sometimes referred to as a "silica nanoparticle" simply.

Considering a working-effect that a site of the fluorescent substance-encapsulated nanoparticle, at which the fluorescent substance-encapsulated nanoparticle may undergo non-specific adsorption because of the composition of its matrix, is blocked by the use of the nanoparticle encapsulating no fluorescent substance, it is preferable that the matrix of the fluorescent substance-encapsulated nanoparticle and the matrix of the nanoparticle encapsulating no fluorescent substance are the same as each other in composition (that is, those nanoparticles are synthesized from the same raw material). However, if equal blocking ability or higher blocking ability is obtained, the compositions of the matrices of those nanoparticles do not need to be the same as each other. Further, plural different compositions can be used without any problem, and moreover, such nanoparticles may be used in combination with hitherto used blocking agents such as BSA.

The fluorescent substance-encapsulated nanoparticles for use in the present invention can be prepared by publicly known processes. Silica nanoparticles encapsulating an organic fluorescent dye can be prepared by referring to, for example, synthesis of FITC-encapsulated silica nanoparticles, which is described in Langmuir, Vol. 8, p. 2921 (1992). By the use of desired organic fluorescent dyes instead of FITC, various organic fluorescent dye-encapsulated silica nanoparticles can be synthesized.

Silica nanoparticles encapsulating semiconductor nanoparticles can be prepared by referring to synthesis of CdTe-encapsulated silica nanoparticles, which is described in New Journal of Chemistry, Vol. 33, p. 561 (2009).

Melamine nanoparticles encapsulating an organic fluorescent dye can be prepared by referring to, for example, synthesis of melamine nanoparticles using a fluorescent brightener, which is described in Japanese Patent Laid-Open Publication No. 62-68811 (1987). By the use of desired organic fluorescent dyes instead of the fluorescent brightener, various organic fluorescent dye-encapsulated melamine nanoparticles can be synthesized.

Polystyrene nanoparticles encapsulating an organic fluorescent dye can be prepared by using, for example, a copolymerization method using an organic dye having a polymerizable functional group, which is described in U.S. Pat. No. 4,326,008 (1982), or a method of impregnation of polystyrene nanoparticles with an organic fluorescent dye, which is described in U.S. Pat. No. 5,326,692 (1992).

Polymer nanoparticles encapsulating semiconductor nanoparticles can be prepared by referring to, for example, a method of impregnation of polystyrene nanoparticles with semiconductor nanoparticles, which is described in Nature Biotechnology, Vol. 19, p. 631 (2001).

In such an impregnation method, the polystyrene nanoparticles are swollen in a solvent to impregnate them with a fluorescent substance, and then they are shrunk in water, so that the fluorescent substance once incorporated into the polystyrene nanoparticles is hardly diffused outside the polystyrene nanoparticles even if the polystyrene nanoparticles are dispersed in different water (aqueous solution).

On the other hand, the process for producing the nanoparticles encapsulating no fluorescent substance is, for example, the same production process as the aforesaid process for producing the fluorescent substance-encapsulated nanoparticles except for using (adding) no fluorescent substance.

In the nanoparticles used for the fluorescent substance-encapsulated nanoparticles and the nanoparticles encapsulating no fluorescent substance, it is preferable that at least a part of their particle surfaces, desirably all of them, are coated with the same organic molecules that are hardly adsorbed on a biological substance. The organic molecules that are hardly adsorbed on a biological substance are organic molecules (preferably organic polymers) which do not have at least such ability that they themselves are specifically bonded to some biological substance and which are not non-specifically bonded either or are hardly adsorbed, and examples thereof include polyethylene glycol [PEG], polymethyl methacrylate (PMMA) and polyvinyl alcohol (PVA).

Considering a working-effect that a site of the fluorescent substance-encapsulated nanoparticle, at which the fluorescent substance-encapsulated nanoparticle may undergo non-specific adsorption because of the organic molecule for coating its surface, is blocked by the use of the nanoparticle encapsulating no fluorescent substance, the organic molecule for coating the fluorescent substance-encapsulated nanoparticle and the organic molecule for coating the nanoparticle encapsulating no fluorescent substance are preferably the same as each other (that is, coating is preferably carried out using the same substance). However, if equal blocking ability or higher blocking ability is obtained, those organic molecules do not need to be the same as each other. As described later, in the fluorescent substance-encapsulated nanoparticles, biological substance-recognizing molecules (e.g., antibody) are sometimes bonded to a part of such organic molecules (e.g., PEG) that modify the particle surfaces. However, the "organic molecules to which biological substance-recognizing molecules have been bonded" are being distinguished from the "organic molecules that are hardly adsorbed on a biological substance" in the above description.

In the nanoparticles used for the fluorescent substance-encapsulated nanoparticles and the nanoparticles encapsulating no fluorescent substance, the mean particle diameter is not specifically restricted, but it is about 30 to 800 nm. Although the coefficient of variation indicating dispersion of particle diameters is not specifically restricted, it is preferably not more than about 20%.

In the present invention, the mean particle diameter of the nanoparticles is a value determined in the following manner. Using a scanning electron microscope [SEM], an electron photomicrograph is taken, and sectional areas of 1,000 nanoparticles are measured. When the measured values are regarded as areas of the corresponding circles, the diameters of the circles are determined as particle diameters, and an arithmetic mean of the particle diameters is taken to be a mean particle diameter. The coefficient of variation is also a value calculated from a particle diameter distribution of 1,000 particles.

Considering a working-effect that a site of the fluorescent substance-encapsulated nanoparticle, at which the fluorescent substance-encapsulated nanoparticle may undergo non-specific adsorption because of its size, is blocked by the use of the nanoparticle encapsulating no fluorescent substance, the difference between the mean particle diameter of the fluorescent substance-encapsulated nanoparticles and the mean particle diameter of the nanoparticles encapsulating no fluorescent substance is preferably not more than 25%, more preferably not more than 5%. When the mean particle diameter of the fluorescent substance-encapsulated nanoparticles is represented by X (nm) and the mean particle diameter of the nanoparticles encapsulating no fluorescent substance is represented by Y (nm), the difference between the mean particle diameters can be calculated from the formula of $|(X-Y)/X|\times100(\%)$.

Bonding Between Biological Substance-Recognizing Molecules and Fluorescent Substance-Encapsulated Nanoparticles The biological substance-recognizing molecules for use in the present invention are molecules which recognize a targeted specific biological substance and are specifically bonded to and/or specifically react with the biological substance.

Examples of the biological substances capable of becoming targets in the present invention include nucleotide chain, protein, lipid and sugar chain, which are derived from living body. Accordingly, as examples of the biological substance-recognizing molecules, there can be mentioned molecules which are specifically bonded to and/or specifically react with those biological substances, such as nucleotide chain (in the case where the biological substance is nucleotide chain or the like having complimentary base sequence), antibody (in the case where the biological substance is protein or the like that becomes antigen) and lectin (in the case where the biological substance is sugar chain or the like that similarly becomes antigen). More specifically, there can be mentioned an anti-HER2 antibody specifically bonded to HER2 that is protein present on a cell surface, an anti-ER antibody specifically bonded to an estrogen receptor [ER] present in a cell nucleus and an anti-actin antibody specifically bonded to actin that forms a cytoskeleton. Of these, the anti-HER2 antibody and the anti-ER antibody are preferable from the viewpoint that they can be used for the selection of medication for breast cancer.

The embodiment of bonding between the biological substance-recognizing molecule and the fluorescent substance-encapsulated nanoparticle is not specifically restricted, and examples thereof include covalent bonding, ionic bonding, hydrogen bonding, coordinate bonding, physical adsorption and chemical adsorption. From the viewpoint of bonding stability, bonding of high bond strength, such as covalent bonding, is preferable.

As a spacer, an organic molecule to connect the biological substance-recognizing molecule to the fluorescent substance-encapsulated nanoparticle may be present. For example, in order to inhibit non-specific adsorption on a biological substance, a polyethylene glycol chain can be used, and specific examples thereof include commercial products such as "SM(PEG)$_{12}$" manufactured by Thermo Scientific. A polyethylene glycol [PEG] chain itself, which is not bonded to the biological substance-recognizing molecule, also functions as such an "organic molecule hardly adsorbed on a biological substance" as previously described.

For bonding the biological substance-recognizing molecules to the fluorescent substance-encapsulated silica nanoparticles, the same method can be applied to any of the case where an organic fluorescent dye is used as the fluorescent substance and the case where semiconductor nanoparticles are used as the fluorescent substance. For example, a silane coupling agent that is a compound widely used for bonding an inorganic substance and an organic substance to each other can be used. This silane coupling agent is a compound having, at one end of a molecule, an alkoxysilyl group that gives a silanol group through hydrolysis, and having, at the other end, a functional group, such as carboxyl group, amino group, epoxy group or aldehyde group, and is bonded to an inorganic substance through an oxygen atom of the silanol group. Specifically, there can be mentioned mercaptopropyltriethoxysilane, glycidoxypropyltriethoxysilane, aminopropyltriethoxysilane, a silane coupling agent having polyethylene glycol chain (e.g., "PEG-silane no. SIM6492.7" manufactured by Gelest), etc. These may be used singly or may be used in combination, as the silane coupling agents.

As the procedure of the reaction of the fluorescent substance-encapsulated silica nanoparticles with the silane coupling agent, a publicly known procedure can be used. For example, the fluorescent substance-encapsulated silica nanoparticles obtained are dispersed in pure water, then aminopropyltriethoxysilane is added, and they are allowed to react with each other at room temperature for 12 hours. After the reaction is completed, centrifugation or filtration is carried out, whereby fluorescent substance-encapsulated silica nanoparticles whose surfaces have been modified with aminopropyl groups can be obtained. Subsequently, by allowing the amino group and a carboxyl group in the antibody to react with each other, the antibody can be bonded to the fluorescent substance-encapsulated silica nanoparticles through the amide bonds. A condensation agent such as EDC [1-ethyl-3[3-dimethylaminopropyl]carbodiimide hydrochloride] (manufactured by Pierce) can be also used, when needed.

If necessary, a linker compound having a site capable of being directly bonded to the organic molecule-modified fluorescent substance-encapsulated silica nanoparticle and a site capable of being bonded to the biological substance-recognizing molecule can be used. For example, if sulfo-SMCC [sulfosuccinimidyl 4[N-maleimidomethyl]-cyclohexane-1-carboxylate] (manufactured by Pierce) having both of a site that selectively reacts with an amino group and a site that selectively reacts with a mercapto group is used, the amino group of the fluorescent substance-encapsulated silica nanoparticles having been modified with aminopropyltriethoxysilane and the mercapto group in the antibody are bonded to each other, whereby fluorescent substance-encapsulated silica nanoparticles to which the antibody has been bonded can be prepared.

For bonding the biological substance-recognizing molecules to the fluorescent substance-encapsulated melamine nanoparticles, the same procedure can be applied to any of the case where an organic fluorescent dye is used as the fluorescent substance and the case where semiconductor nanoparticles are used as the fluorescent substance. For example, by the use of EDC or sulfo-SMCC, fluorescent substance-encapsulated melamine nanoparticles to which an antibody has been bonded through the amino group present on the melamine nanoparticles can be prepared.

For bonding the biological substance-recognizing molecules to the fluorescent substance-encapsulated polystyrene nanoparticles, the same procedure can be applied to any of the case where an organic fluorescent dye is used as the fluorescent substance and the case where semiconductor nanoparticles are used as the fluorescent substance. For example, by the use of the aforesaid impregnation method, polystyrene nanoparticles having a functional group such as amino group are impregnated with an organic fluorescent dye or semiconductor nanoparticles, whereby fluorescent substance-encapsulated polystyrene nanoparticles having a functional group such as amino group can be obtained. Then, by the use of EDC or sulfo-SMCC, fluorescent substance-encapsulated polystyrene nanoparticles to which an antibody has been bonded can be prepared.

Procedure of Detection Method

The present invention is a detection method using a specific color former and a specific blocking agent in combination, as described above, and is advantageous for a publicly known method for fluorescent staining of a tissue section. Although the tissue section is composed of a biological substance, it is not limited to a pathological tissue section, and it can be also applied to cell staining.

The preparation process for a tissue section to which the detection method of the present invention is applicable is not specifically restricted, and a tissue section prepared by a publicly known process can be used.

The following steps included in the detection method of the present invention will be described in order hereinafter.

(1) Deparaffinization Step

A tissue section is immersed in xylene contained in a container to remove paraffin. Although the temperature is not specifically restricted, this step can be carried out at room temperature. The immersion time is preferably 3 to 30 minutes. During immersion, xylene may be exchanged, when needed.

Subsequently, this section is immersed in ethanol contained in a container to remove xylene. Although the temperature is not specifically restricted, this step can be carried out at room temperature. The immersion time is preferably 3 to 30 minutes. During immersion, ethanol may be exchanged, when needed.

Subsequently, this section is immersed in water contained in a container to remove ethanol. Although the temperature is not specifically restricted, this step can be carried out at room temperature. The immersion time is preferably 3 to 30 minutes. During immersion, water may be exchanged, when needed.

(2) Activation Treatment Step

In accordance with a publicly known method, activation treatment of a specific biological substance is carried out. The activation conditions are not specifically defined, but as an activation liquid, a solution containing a 0.01 M citrate buffer solution (pH 6.0), a 1 mM EDTA solution (pH 8.0), 5% urea, a 0.1 M tris-hydrochloric acid buffer solution or the like can be used. As a heating apparatus, an autoclave, a microwave, a pressure pan, a water bath or the like can be used. Although the temperature is not specifically restricted, this step can be carried out at room temperature. This step can be carried out at a temperature of 50 to 130° C. for a period of 5 to 30 minutes.

Subsequently, the section obtained after the activation treatment is immersed in water and PBS contained in a container to carry out washing. Although the temperature is not specifically restricted, this step can be carried out at room temperature. The immersion time is preferably 3 to 30 minutes. During immersion, PBS may be exchanged, when needed.

(3) Staining Step Using Biological Substance-Recognizing Molecule-Bonded Fluorescent Substance-Encapsulated Nanoparticles (Color Former)

In this hystochemical staining step (3), a phosphate buffered saline [PBS] dispersion of fluorescent substance-encapsulated nanoparticles to which biological substance-recognizing molecules have been bonded is first prepared, then this dispersion is placed on a section, and a reaction with a specific biological substance is carried out. Although the temperature is not specifically restricted, this step can be carried out at room temperature. The reaction time is preferably 5 minutes to 24 hours. As an example of the solvent for stably maintaining environment suitable for the reaction of the specific biological substance with the biological substance-recognizing molecules, PBS is given above, but not only PBS but also a phosphate buffer solution, a Tris buffer solution, a MES buffer solution, a citric acid-phosphoric acid buffer solution, etc. can be used.

In the present invention, prior to staining with the florescent material-encapsulated nanoparticles, a blocking agent is dropwise added. As the blocking agent, nanoparticles having no fluorescence property, namely, nanoparticles encapsulating no fluorescent substance are used. In a preferred embodiment, the composition of the matrix of the nanoparticles having no fluorescence property and the composition of the matrix of the fluorescent substance-encapsulated nanoparticles are the same as each other. It is more preferable that the difference between the mean particle diameters of those nanoparticles is not more than 25%, and it is particularly preferable that the surfaces of the nanoparticles having no fluorescence property are coated with polyethylene glycol.

Although the amount of the blocking agent is not specifically restricted, it is generally 0.5 to 10 times as much as the color former. The blocking agent related to the present invention may be used singly, or may be used in combination with a publicly known blocking agent such as BSA or skim milk.

Subsequently, the section obtained after staining is immersed in PBS contained in a container to remove unreacted fluorescent substance-encapsulated nanoparticles. In the PBS solution, a surface active agent such as Tween 20 may be contained. Although the temperature is not specifically restricted, this step can be carried out at room temperature. The immersion time is preferably 3 to 30 minutes. During immersion, PBS may be exchanged, when needed.

(4) Fixing Treatment Step

The fixing treatment step necessary in the present invention is a step for fixing the labeled probe biological substance, which has been introduced in the above staining step (3), to the tissue section.

Examples of the fixing treatment solutions for use in the present invention include crosslinking agents and cell membrane-permeable substances, such as formalin, paraformaldehyde, glutaric aldehyde, acetone, ethanol and methanol.

In the present invention, the fixing treatment can be carried out by a hitherto publicly known method. Specifically, the fixing treatment can be carried out by immersing the stained tissue section obtained in the hystochemical staining step (3) in such a fixing treatment solution as above. For example, the fixing treatment can be carried out by immersing the stained tissue section obtained in the histochemical staining step (3) in a dilute paraformaldehyde aqueous solution for about several minutes to several hours.

(5) Step of Observation Under Fluorescence Microscope

The section obtained as above is observed using a fluorescence microscope, and the level of expression of the specific biological substance can be measured on the basis of the number of luminous points and the emission luminance. An excitation light source and an optical filter for fluorescence detection, which meet the absorption maximum wavelength and the fluorescence wavelength of the fluorescent substance used, can be appropriately selected by a person skilled in the art.

Measurement of the number of luminous points and the emission luminance can be carried out by the use of image analysis software, such as Image J that is analysis software opened to the public or total luminous point automatic measurement software G-Count manufactured by G-Angstrom K.K.

EXAMPLES

The present invention will be described in more detail with reference to the following examples, but the present invention is in no way limited to those examples.

Production of Blocking Agent

As blocking agents, several kinds of "nanoparticles encapsulating no fluorescent substance" were produced in the following manner. These particles differ from one another in composition of matrix, mean particle diameter and whether the particles are coated with polyethylene glycol [PEG] or not.

Production Example 1

Polystyrene Nanoparticles Coated with PEG

Step (1-1): A phosphate buffered saline [PBS] containing 2 mM of ethylenediaminetetraacetic acid [EDTA] was used for 1 mg of polystyrene nanoparticles ("micromer (registered trademark) 01-01-102" manufactured by Micromod, mean particle diameter: 100 nm) to adjust the concentration of the polystyrene nanoparticle to 3 nM.

Step (1-2): The solution adjusted in the step (1-1) was mixed with "SM(PEG)$_{12}$" (succinimidyl-[(N-maleomidopropionamid)-dodecaethyleneglycol]ester manufactured by Thermo Scientific), and reaction was carried out for 3 hours.

Step (1-3): The reaction mixture of the step (1-2) was subjected to centrifugation of 10,000×g for 60 minutes, and the supernatant liquid was removed.

Step (1-4): Washing consisting of adding PBS containing 2 mM of EDTA to the precipitate of the step (1-3) to disperse the precipitate, subjecting the dispersion to centrifugation again and removing the supernatant liquid was carried out. Washing of the same procedure as above was further carried out twice. Thereafter, the resulting precipitate was redispersed in 500 µL of PBS. As a result, polystyrene nanoparticles coated with PEG and encapsulating no fluorescent substance were obtained.

Production Example 2

Melamine Nanoparticles

Step (2-1): 15 g of melamine, 29 g of 37% formalin and 1.5 g of a 28% ammonia aqueous solution were mixed to adjust the mixture to pH 8.

Step (2-2): With stirring the mixed solution of the step (2-1), the temperature was raised to 70° C., and reaction was carried out for 30 minutes to obtain an initial condensate.

Step (2-3): In 22 ml of water, 0.12 ml of "Neopelex G-15" (manufactured by Kao Corporation) was dissolved, and four samples heated to 90° C. were prepared.

Step (2-4): Into each of the samples of the step (2-3), 1 g of the initial condensate obtained in the step (2-2) was introduced, and then, to the resulting mixtures, dodecylbenzenesulfonic acid was added in amounts of 0.5 mL, 0.7 mL, 0.85 mL and 0.9 mL, respectively, followed by stirring for 6 hours.

Step (2-5): Each of the reaction mixtures of the step (2-4) was subjected to centrifugation of 10,000×g for 60 minutes, then the supernatant liquid was removed, thereafter ethanol was added to disperse the precipitate, and the dispersion was subjected to centrifugation again. Washing with ethanol and washing with pure water were each carried out once again by the same procedure as above.

Nanoparticles encapsulating no fluorescent substance obtained as above were observed by a scanning electron microscope [SEM] (S-800 type manufactured by Hitachi, Ltd.), and as a result, the mean particle diameters (coefficients of variation) of the nanoparticles were 72 nm (10.5%), 83 nm (11.3%), 91 nm (9.5%) and 98 nm (9.3%).

Production Example 3

Melamine Nanoparticles Coated with PEG

Melamine nanoparticles coated with PEG were produced in the same manner as in Production Example 1, except that the melamine nanoparticles having a mean particle diameter of 98 nm obtained in Production Example 2 were used instead of the polystyrene nanoparticles.

Production Example 4

Silica Nanoparticles

Step (4-1): 40 mL of ethanol and 9.7 mL of 14% aqueous ammonia were mixed.

Step (4-2): With stirring the mixed liquid of the step (4-1), 400 μL (1.796 mmol) of tetraethoxysilane was added to the liquid. Stirring was carried out for 7 hours from the beginning of the addition.

Step (4-3): The reaction mixture of the step (4-2) was subjected to centrifugation of 10,000×g for 60 minutes, and the supernatant liquid was removed. Then, ethanol was added to disperse the precipitate, and the dispersion was subjected to centrifugation again. Washing with ethanol and washing with pure water were each carried out once again by the same procedure as above.

Nanoparticles encapsulating no fluorescent substance obtained as above were subjected to SEM observation, and as a result, the mean particle diameter was 69 nm, and the coefficient of variation was 17%.

Further, three kinds of silica nanoparticles different in mean particle diameter were produced in the same manner as in the steps (4-1) to (4-3), except that the amount of the 14% aqueous ammonia was changed to 10 mL, 11.5 mL or 13 mL from 9.7 mL in the step (4-1). The mean particle diameters (coefficients of variation) of the resulting silica nanoparticles were 79 nm (100), 88 nm (12.6%) and 99 nm (11.3%).

Production Example 5

Silica Nanoparticles Coated with PEG

Step (5-1): In 5 mL of pure water, 1 mg of the silica nanoparticles having a mean particle diameter of 99 nm obtained in Production Example 4 were dispersed. Then, 100 μL of aminopropyltriethoxysilane was added, followed by stirring at room temperature for 12 hours.

Step (5-2): The reaction mixture of the step (5-1) was subjected to centrifugation of 10,000×g for 60 minutes, and the supernatant liquid was removed.

Step (5-3): To the precipitate of the step (5-2), ethanol was added to disperse the precipitate, and the dispersion was subjected to centrifugation again. Washing with ethanol and washing with pure water were each carried out once again by the same procedure as above.

The resulting amino group-modified silica nanoparticles were subjected to FT-IR measurement. As a result, absorption derived from amino group could be observed, and it was confirmed that the nanoparticles had been modified to have amino groups.

Then, silica nanoparticles coated with PEG and encapsulating no fluorescent substance were produced in the same manner as in Production Example 1, except that the amino group-modified silica nanoparticles obtained in the step (5-3) were used instead of the polystyrene nanoparticles.

Production of Color Former

As color formers, four kinds of "fluorescent substance-encapsulated nanoparticles to whose particle surfaces biological substance-recognizing molecules that specifically recognize a specific biological substance had been bonded" were produced. They were all coated with PEG, and to their particle surfaces an anti-HER2 antibody was bonded, but they differed from one another in type of fluorescent substance, composition of matrix and mean particle diameter.

Production Example 6

Color Former <A>

Step (6-1): In a mixed solvent of water and ethanol (water:ethanol=2:8), 10 g of polystyrene nanoparticles ("micromer (registered trademark) 01-01-102" manufactured by Micromod, mean particle diameter: 10 nm) were dispersed, and the dispersion was stirred at room temperature for 3 hours.

Step (6-2): To the dispersion of the step (6-1), 1 mg (0.00126 mmol) of Cy5 (manufactured by GE Healthcare Japan Corporation) was added, and they were stirred at 60° C. for 12 hours.

Step (6-3): The reaction mixture of the step (6-2) was subjected to centrifugation of 10,000×g for 60 minutes, and the supernatant liquid was removed. Then, thereto was added ethanol to disperse the precipitate, and the dispersion was subjected to centrifugation again. Washing with ethanol and washing with pure water were each carried out once again by the same procedure as above. As a result, fluorescent substance-encapsulated polystyrene nanoparticles were obtained.

Step (6-4): PBS containing 2 mM of EDTA was used for 1 mg of the fluorescent substance-encapsulated polystyrene nanoparticles of the step (6-3) to adjust the concentration of the nanoparticles to 3 nM.

Step (6-5): The solution of the step (6-4) was mixed with "SM (PEG)$_{12}$" so that the final concentration might become 10 mM, and reaction was carried out for 3 hours.

Step (6-6): The reaction mixture of the step (6-5) was subjected to centrifugation of 10,000×g for 60 minutes, and the supernatant liquid was removed.

Step (6-7): To the precipitate of the step (6-6), PBS containing 2 mM of EDTA was added to disperse the precipitate, and the dispersion was subjected to centrifugation again. Washing of the same procedure as above was carried out three times. Finally, the resulting precipitate was redispersed in 500 μL of PBS. As a result, a particle dispersion of polystyrene nanoparticles coated with PEG was obtained.

Step (6-8): In 100 μL of PBS, 100 μg of an anti-HER2 antibody was dissolved, and to the solution, 1M dithiothreitol [DTT] was added, followed by reaction for 30 minutes.

Step (6-9): From the reaction mixture of the step (6-8), excess DTT was removed by a gel filtration column to obtain a reduced anti-HER2 antibody solution.

Step (6-10): The particle dispersion of the step (6-7) and the reduced anti-HER2 antibody solution of the step (6-9) were mixed in PBS, and reaction was carried out for 1 hour.

Step (6-11): To the reaction liquid of the step (6-10), 4 μL of 10 mM mercaptoethanol was added to terminate the reaction.

Step (6-12): The reaction mixture of the step (6-11) was subjected centrifugation of 10,000×g for 60 minutes, and the supernatant liquid was removed. Thereafter, PBS containing 2 mM of EDTA was added to disperse the precipitate, and the dispersion was subjected to centrifugation again. Washing of the same procedure as above was carried out three times. Finally, the resulting precipitate was redispersed in 500 μL of PBS to obtain a particle dispersion of fluorescent substance (Cy5)-encapsulated polystyrene nanoparticles (namely, color former <A>) to which the anti-HER2 antibody had been bonded and which had been coated with PEG was obtained.

Production Example 7

Color Former <B>

Step (7-1): 15 g of melamine, 29 g of 37% formalin and 1.5 g of a 28% ammonia aqueous solution were mixed to adjust the mixture to pH 8.

Step (7-2): With stirring the mixture of the step (7-1), the temperature was raised to 70° C., and reaction was carried out for 30 minutes to obtain an initial condensate.

Step (7-3): In 22 mL of water, 0.12 ml of "Neopelex G-15" and 1 mg of Cy5 (0.00126 mmol) were dissolved, and the temperature was raised to 90° C.

Step (7-4): To the solution of the step (7-3), 1 g of the initial condensate of the step (7-2) was introduced, and thereafter, 0.93 mL of dodecylbenzenesulfonic acid was added, followed by stirring for 6 hours.

Step (7-5): The reaction mixture of the step (7-4) was subjected to centrifugation of 10,000×g for 60 minutes, and the supernatant liquid was removed. Then, thereto was added ethanol to disperse the precipitate, and the dispersion was subjected to centrifugation again. Washing with ethanol and washing with pure water were each carried out once again by the same procedure as above. The fluorescent substance-encapsulated melamine nanoparticles obtained as above were observed by SEM, and as a result, the mean particle diameter was 97 nm, and the coefficient of variation was 10%.

Then, a particle dispersion of fluorescent substance (Cy5)-encapsulated melamine nanoparticles (namely, color former <B>) to which the anti-HER2 antibody had been bonded and which had been coated with PEG was produced in the same manner as in the steps (6-4) to (6-12), except that the fluorescent substance-encapsulated melamine nanoparticles were used instead of the fluorescent substance-encapsulated polystyrene nanoparticles in the step (6-4).

Production Example 8

Color Former <C>

Step (8-1): 1 mg (0.00126 mmol) of an N-hydroxysuccinimide ester derivative of Cy5 (manufactured by GE Healthcare Japan Corporation) was mixed with 420 µL (1.796 mmol) of tetraethoxysilane.

Step (8-2): 40 mL of ethanol was mixed with 13.8 mL of 14% aqueous ammonia.

Step (8-3): With stirring the mixed liquid of the step (8-2) at room temperature, the mixed liquid of the step (8-1) was added thereto. Stirring was carried out for 12 hours from the beginning of the addition.

Step (8-4): The reaction mixture of the step (8-3) was subjected to centrifugation of 10,000×g for 60 minutes, and the supernatant liquid was removed. Then, thereto was added ethanol to disperse the precipitate, and the dispersion was subjected to centrifugation again. Washing with ethanol and washing with pure water were each carried out once again by the same procedure as above. The fluorescent substance-encapsulated silica nanoparticles obtained as above were observed by SEM, and as a result, the mean particle diameter was 99 nm, and the coefficient of variation was 12%.

Step (8-5): Fluorescent substance-encapsulated silica nanoparticles modified with amino groups were produced in the same manner as in the steps (5-1) to (5-3), except that the fluorescent substance-encapsulated silica nanoparticles of the step (8-4) were used instead of the silica nanoparticles encapsulating no fluorescent substance in the step (5-1).

Step (8-6): Fluorescent substance-encapsulated silica nanoparticles coated with PEG were produced in the same manner as in Production Example 1, except that the amino group-modified fluorescent substance-encapsulated silica nanoparticles produced as above were used instead of the polystyrene nanoparticles.

Step (8-7): The particle dispersion of the step (8-6) and the reduced anti-HER2 antibody solution of the step (6-9) were mixed in PBS, and reaction was carried out for 1 hour.

Step (8-8): To the reaction liquid of the step (8-7), 4 µL of 10 mM mercaptoethanol was added to terminate the reaction.

Step (8-9): The reaction mixture of the step (8-8) was subjected to centrifugation of 10,000×g for 60 minutes, and the supernatant liquid was removed. Thereafter, PBS containing 2 mM of EDTA was added to disperse the precipitate, and the dispersion was subjected to centrifugation again. Washing of the same procedure as above was carried out three times. Finally, the resulting precipitate was redispersed in 500 µL of PBS to obtain a particle dispersion of fluorescent substance (Cy5)-encapsulated silica nanoparticles (mean particle diameter: 135 nm) (namely, color former <C>) to which the anti-HER2 antibody had been bonded and which had been coated with PEG.

Production Example 9

Color Former <D>

Step (9-1): 10 µL of a decane dispersion of CdSe/ZnS ("Qdot 655" manufactured by Invitrogen Japan K.K.) having an emission wavelength of 655 nm and 40 µL of tetraethoxysilane were mixed.

Step (9-2): 4 mL of ethanol and 2.5 mL of 14% aqueous ammonia were mixed.

Step (9-3): With stirring the mixed liquid of the step (9-2) at room temperature, the mixed liquid of the step (9-1) was added thereto. Stirring was carried out for 12 hours from the beginning of the addition.

Step (9-4): The reaction mixture was subjected to centrifugation of 10,000×g for 60 minutes, and the supernatant liquid was removed. Then, thereto was added ethanol to disperse the precipitate, and the dispersion was subjected to centrifugation again. Washing with ethanol and washing with pure water were each carried out once again by the same procedure as above. The resulting fluorescent substance-encapsulated silica nanoparticles were subjected to SEM observation, and as a result, the mean particle diameter was 130 nm, and the coefficient of variation was 13%.

Then, a particle dispersion of fluorescent substance (CdSe/ZnS)-encapsulated silica nanoparticles (mean particle diameter: 101 nm) (namely, color former <D>) to which the anti-HER2 antibody had been bonded and which had been coated with PEG was produced in the same manner as in the steps (8-5) to (8-9), except that the fluorescent substance-encapsulated silica nanoparticles of the step (9-4) were used instead of the fluorescent substance-encapsulated silica nanoparticles of the step (8-4) in the step (8-5).

Performance of Detection Method in Immunohistological Staining of HER2

Comparative Example

Use of BSA as Blocking Agent

Using each of the color formers <A> to <D> obtained in Production Examples 6 to 9 as a color former and using a section adjacent to human breast tissue, judgment result of which had been already known by DAB staining, immunohystological staining was carried out in accordance with the following steps. As the section, a tissue array slide "CB-A712" manufactured by Cosmo Bio Co., Ltd. was used.

Step (C-1): In xylene contained in a container, the above section was immersed for 30 minutes. During the immersion, xylene was exchanged three times.

Step (C-2): This section was immersed in ethanol contained in a container for 30 minutes. During the immersion, ethanol was exchanged three times.

Step (C-3): This section was immersed in water contained in a container for 30 minutes. During the immersion, water was exchanged three times.

Step (C-4): This section was immersed in a 10 mM citrate buffer solution (pH 6.0) for 30 minutes.

Step (C-5): Autoclave treatment was carried out at 121° C. for 10 minutes.

Step (C-6): In PBS contained in a container, the section having been subjected to autoclave treatment was immersed for 30 minutes.

Step (C-7): On the tissue, 1% BSA-containing PBS was placed as a blocking agent, and they were allowed to stand for 1 hour.

Step (C-8): On the sections, the color formers <A> to <D> having been diluted to 0.05 nM with 1% BSA-containing PBS were placed, respectively, and they were allowed to stand for 3 hours.

Step (C-9): In PBS contained in a container, the sections having been subjected to staining were each immersed for 30 minutes.

Step (C-10): On each of the sections, "Aquatex" manufactured by Merck Chemicals Ltd. was dropped, and then, a cover glass was placed to seal it.

Observation under fluorescence microscope: Subsequently, the stained sections were observed using a fluorescence microscope "BX53" manufactured by Olympus Corporation to specify expression of the desired biological substance, namely, HER2, from the number of luminous points, and after binarization treatment using Image J and noise removal treatment, luminous point measurement was carried out to measure the number of luminous points based on 10 cells. The measurement of luminous points was carried out with regard to 20 spots on the slide.

Example 1

Polystyrene Nanoparticles (Mean Particle Diameter: 70 nm) as Blocking Agent

Immunohistological staining of sections was carried out in the same manner as in Comparative Example, except that a polystyrene nanoparticle ("3070A" manufactured by Thermo Fisher Scientific, mean particle diameter: 70 nm)-containing PBS dispersion was used instead of the 1% BSA-containing PBS. Then, observation under fluorescence microscope was carried out.

Example 2

Polystyrene Nanoparticles (Mean Particle Diameter: 80 nm) as Blocking Agent

Immunohistological staining of sections was carried out in the same manner as in Comparative Example, except that a polystyrene nanoparticle ("3080A" manufactured by Thermo Fisher Scientific, mean particle diameter: 80 nm)-containing PBS dispersion was used instead of the 1% BSA-containing PBS. Then, observation under fluorescence microscope was carried out.

Example 3

Polystyrene Nanoparticles (Mean Particle Diameter: 90 nm) as Blocking Agent

Immunohistological staining of sections was carried out in the same manner as in Comparative Example, except that a polystyrene nanoparticle ("3090A" manufactured by Thermo Fisher Scientific, mean particle diameter: 90 nm)-containing PBS dispersion was used instead of the 1% BSA-containing PBS. Then, observation under fluorescence microscope was carried out.

Example 4

Polystyrene Nanoparticles (Mean Particle Diameter: 100 nm) as Blocking Agent

Immunohistological staining of sections was carried out in the same manner as in Comparative Example, except that a polystyrene nanoparticle ("micromer (registered trademark) 01-01-102" manufactured by Micromod, mean particle diameter: 100 nm)-containing PBS dispersion was used instead of the 1% BSA-containing PBS. Then, observation under fluorescence microscope was carried out.

Example 5

PEG-coated Polystyrene Nanoparticles (Mean Particle Diameter: 100 nm) as Blocking Agent Immunohistological staining of sections was carried out in the same manner as in Comparative Example, except that the PEG-coated polystyrene nanoparticle-containing PBS dispersion obtained in Production Example 1 was used instead of the 1% BSA-containing PBS. Then, observation under fluorescence microscope was carried out.

Example 6

Melamine Nanoparticles (Mean Particle Diameter: 72 nm) as Blocking Agent

Immunohistological staining of sections was carried out in the same manner as in Comparative Example, except that the melamine nanoparticle (mean particle diameter: 72 nm)-containing PBS dispersion obtained in Production Example 2 was used instead of the 1% BSA-containing PBS. Then, observation under fluorescence microscope was carried out.

Example 7

Melamine Nanoparticles (Mean Particle Diameter: 83 nm) as Blocking Agent

Immunohistological staining of sections was carried out in the same manner as in Comparative Example, except that the melamine nanoparticle (mean particle diameter: 82 nm)-containing PBS dispersion obtained in Production Example 2 was used instead of the 1% BSA-containing PBS. Then, observation under fluorescence microscope was carried out.

Example 8

Melamine Nanoparticles (Mean Particle Diameter: 91 nm) as Blocking Agent

Immunohistological staining of sections was carried out in the same manner as in Comparative Example, except that the melamine nanoparticle (mean particle diameter: 91 nm)-containing PBS dispersion obtained in Production Example 2 was used instead of the 1% BSA-containing PBS. Then, observation under fluorescence microscope was carried out.

Example 9

Melamine Nanoparticles (Mean Particle Diameter: 98 nm) as Blocking Agent

Immunohistological staining of sections was carried out in the same manner as in Comparative Example, except that the melamine nanoparticle (mean particle diameter: 98 nm)-containing PBS dispersion obtained in Production Example 2 was used instead of the 1% BSA-containing PBS. Then, observation under fluorescence microscope was carried out.

Example 10

PEG-coated Melamine Nanoparticles (Mean Particle Diameter: 98 nm) as Blocking Agent Immunohistological staining of sections was carried out in the same manner as in Comparative Example, except that the PEG-coated melamine nanoparticle-containing PBS dispersion obtained in Production Example 3 was used instead of the 1% BSA-containing PBS. Then, observation under fluorescence microscope was carried out.

Example 11

Silica Nanoparticles (Mean Particle Diameter: 69 nm) as Blocking Agent

Immunohistological staining of sections was carried out in the same manner as in Comparative Example, except that the silica nanoparticle (mean particle diameter: 69 nm)-containing PBS dispersion obtained in Production Example 4 was used instead of the 1% BSA-containing PBS. Then, observation under fluorescence microscope was carried out.

Example 12

Silica Nanoparticles (Mean Particle Diameter: 79 nm) as Blocking Agent

Immunohistological staining of sections was carried out in the same manner as in Comparative Example, except that the silica nanoparticle (mean particle diameter: 79 nm)-containing PBS dispersion obtained in Production Example 4 was used instead of the 1% BSA-containing PBS. Then, observation under fluorescence microscope was carried out.

Example 13

Silica Nanoparticles (Mean Particle Diameter: 88 nm) as Blocking Agent

Immunohistological staining of sections was carried out in the same manner as in Comparative Example, except that the silica nanoparticle (mean particle diameter: 88 nm)-containing PBS dispersion obtained in Production Example 4 was used instead of the 1% BSA-containing PBS. Then, observation under fluorescence microscope was carried out.

Example 14

Silica Nanoparticles (Mean Particle Diameter: 99 nm) as Blocking Agent

Immunohistological staining of sections was carried out in the same manner as in Comparative Example, except that the silica nanoparticle (mean particle diameter: 99 nm)-containing PBS dispersion obtained in Production Example 4 was used instead of the 1% BSA-containing PBS. Then, observation under fluorescence microscope was carried out.

Example 15

PEG-Coated Silica Nanoparticles (Mean Particle Diameter: 99 nm) as Blocking Agent Immunohistological staining of sections was carried out in the same manner as in Comparative Example, except that the PEG-coated silica nanoparticle (mean particle diameter: 99 nm)-containing PBS dispersion obtained in Production Example 5 was used instead of the 1% BSA-containing PBS. Then, observation under fluorescence microscope was carried out.

These results are set forth in Table 1. In Table 1, a case where the blocking agent was coated with PEG is represented by "+", a case where the blocking agent was not coated with PEG is represented by "−", when the mean particle diameter of the color former is represented by X (nm) and the mean particle diameter of the blocking agent is represented by Y (nm), a difference in mean particle diameter is calculated from the formula of $\{(X-Y)/X\} \times 100(\%)$, and the number of luminous points is represented by a relative value given when negativity of each of the color formers <A> to <D> of Comparative Example is taken to be 1.

TABLE 1

| | | | | | Color former (anti-HER2 antibody-bonded PEG-coated fluorescent material-encapsulated nanoparticles) | | | | |
|---|---|---|---|---|---|---|---|---|---|
| | Blocking agent | | | | <A> Fluorescent substance = Cy5 Matrix = polystyrene Mean particle diameter = 100 nm | | | <B> Fluorescent substance = Cy5 Matrix = melamine Mean particle diameter = 97 nm | |
| | Composition of matrix of nanoparticles encapsulating no fluorescent substance | PEG coating | Mean particle diameter [nm] | Difference in mean particle diameter | Number of luminous points | | Difference in mean particle diameter | Number of luminous points | |
| | | | | | Positivity | Negativity | | Positivity | Negativity |
| Comparative Example | (BSA) | | | — | 8.5 | 1 | — | 11 | 1 |
| Example 1 | polystyrene | – | 70 | 30% | 14.0 | 0.93 | 28% | 12.5 | 0.77 |
| 2 | | | 80 | 20% | 16.0 | 0.91 | 18% | 13.1 | 0.77 |
| 3 | | | 90 | 10% | 17.3 | 0.80 | 7% | 13.2 | 0.73 |
| 4 | | | 100 | 0% | 18.1 | 0.78 | −3% | 14 | 0.72 |
| 5 | | + | | | 19.2 | 0.72 | | 14.5 | 0.70 |
| 6 | melamine | – | 72 | 28% | 17.8 | 0.59 | 26% | 16.0 | 0.33 |
| 7 | | | 83 | 17% | 18.0 | 0.55 | 14% | 16.2 | 0.30 |
| 8 | | | 91 | 9% | 18.6 | 0.52 | 6% | 16.5 | 0.22 |
| 9 | | | 98 | 2% | 19.7 | 0.37 | −1% | 16.8 | 0.18 |
| 10 | | + | | | 21.0 | 0.31 | | 16.9 | 0.15 |
| 11 | silica | – | 69 | 31% | 14.0 | 0.40 | 29% | 12.4 | 0.42 |
| 12 | | | 79 | 21% | 14.8 | 0.38 | 19% | 12.5 | 0.38 |
| 13 | | | 88 | 12% | 15.9 | 0.33 | 9% | 12.9 | 0.37 |
| 14 | | | 99 | 1% | 16.7 | 0.26 | −2% | 13.2 | 0.33 |
| 15 | | + | | | 17.7 | 0.20 | | 13.5 | 0.32 |

| | | | | | Color former (anti-HER2 antibody-bonded PEG-coated fluorescent material-encapsulated nanoparticles) | | | | |
|---|---|---|---|---|---|---|---|---|---|
| | Blocking agent | | | | <C> Fluorescent substance = Cy5 Matrix = silica Mean particle diameter = 99 nm | | | <D> Fluorescent substance = CdSe/ZnS Matrix = silica Mean particle diameter = 101 nm | |
| | Composition of matrix of nanoparticles encapsulating no fluorescent substance | PEG coating | Mean particle diameter [nm] | Difference in mean particle diameter | Number of luminous points | | Difference in mean particle diameter | Number of luminous points | |
| | | | | | Positivity | Negativity | | Positivity | Negativity |
| Comparative Example | (BSA) | | | — | 9.2 | 1 | — | 3.5 | 1 |
| Example 1 | polystyrene | – | 70 | 29% | 14.5 | 0.92 | 31% | 4.5 | 0.97 |
| 2 | | | 80 | 19% | 14.5 | 0.88 | 21% | 4.6 | 0.95 |
| 3 | | | 90 | 9% | 14.6 | 0.85 | 11% | 4.8 | 0.94 |
| 4 | | | 100 | −1% | 15.0 | 0.82 | 1% | 5.0 | 0.87 |
| 5 | | + | | | 15.2 | 0.78 | | 5.2 | 0.77 |
| 6 | melamine | – | 72 | 27% | 16.0 | 0.65 | 29% | 6.0 | 0.77 |
| 7 | | | 83 | 16% | 16.5 | 0.55 | 18% | 6.2 | 0.72 |
| 8 | | | 91 | 8% | 16.7 | 0.45 | 10% | 6.4 | 0.68 |
| 9 | | | 98 | 1% | 17.0 | 0.41 | 3% | 6.8 | 0.48 |
| 10 | | + | | | 17.2 | 0.32 | | 7.0 | 0.45 |
| 11 | silica | – | 69 | 30% | 15.7 | 0.32 | 32% | 5.2 | 0.41 |
| 12 | | | 79 | 20% | 15.9 | 0.29 | 22% | 5.3 | 0.38 |
| 13 | | | 88 | 11% | 16.2 | 0.28 | 13% | 5.5 | 0.33 |
| 14 | | | 99 | 0% | 17.0 | 0.24 | 2% | 6.0 | 0.28 |
| 15 | | + | | | 17.0 | 0.15 | | 6.8 | 0.25 |

<<Comments>>

From Table 1, it can be seen that nanoparticles encapsulating no fluorescent substance are significantly superior in blocking ability to BSA that is usually used as a blocking agent. The reason is presumed to be that while BSA prevents non-specific adsorption concerning the antigen-antibody reaction, the nanoparticles encapsulating no fluorescent substance can prevent not only non-specific adsorption concerning the antigen-antibody reaction but also non-specific adsorption occurring depending upon size, etc. of nanoparticles by means of steric hindrance between particles.

The invention claimed is:

1. A detection method for a specific biological substance on a tissue section or a fixed cell section, comprising, in this order:
  placing a blocking agent on the tissue section or the fixed cell section; and
  placing a color former on the tissue section or the fixed cell section,
  wherein the color former comprises fluorescent substance-encapsulated nanoparticles having biological substance-recognizing molecules, the biological substance-recognizing molecules specifically recognize the specific biological substance, the biological substance-recognizing molecules are bonded to surfaces of the fluorescent substance-encapsulated nanoparticles, the blocking agent comprises nanoparticles encapsulating no fluorescent substance for preventing the fluorescent substance-encapsulated nanoparticles from being non-specifically adsorbed on a biological substance other than the specific biological substance, at least a part of the surfaces of the fluorescent substance-encapsulated nanoparticles and at least a part of surfaces of the nanoparticles encapsulating no fluorescent substance are each coated with the same organic molecules that are hardly adsorbed on the biological substance, an amount of the nanoparticles encapsulating no fluorescent substance is up to 10 times more than an amount of the fluorescent substance-encapsulated nanoparticles, a difference between a mean particle diameter of the fluorescent substance-encapsulated nanoparticles and a mean particle diameter of the nanoparticles encapsulating no fluorescent substance is not more than 5%, and the organic molecules that are hardly adsorbed on the biological substance are selected from the group consisting of polyethylene glycol (PEG), polymethyl methacrylate (PMMA), and polyvinyl alcohol (PVA).

2. The detection method as claimed in claim 1, wherein a matrix of the fluorescent substance-encapsulated nanoparticles and a matrix of the nanoparticles encapsulating no fluorescent substance have same composition.

* * * * *